United States Patent
Clerc et al.

(10) Patent No.: US 9,801,742 B2
(45) Date of Patent: Oct. 31, 2017

(54) RADIOPAQUE COMPOSITIONS, STENTS AND METHODS OF PREPARATION

(71) Applicant: Boston Scientific Scimed, Inc., Maple Grove, MN (US)

(72) Inventors: Claude O. Clerc, Marlborough, MA (US); F. Anthony Headley, Jr., Atlanta, GA (US); Forrest D. Whitcher, Allston, MA (US); Suresh Gidwani, North Chelmsford, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 566 days.

(21) Appl. No.: 14/295,911

(22) Filed: Jun. 4, 2014

(65) Prior Publication Data

US 2014/0288637 A1   Sep. 25, 2014

Related U.S. Application Data

(63) Continuation of application No. 13/853,181, filed on Mar. 29, 2013, now Pat. No. 8,852,265, which is a continuation of application No. 12/061,379, filed on Apr. 2, 2008, now Pat. No. 8,409,270.

(60) Provisional application No. 60/923,650, filed on Apr. 16, 2007.

(51) Int. Cl.
| | |
|---|---|
| *A61F 2/06* | (2013.01) |
| *A61F 2/88* | (2006.01) |
| *A61F 2/90* | (2013.01) |
| *A61F 2/82* | (2013.01) |

(52) U.S. Cl.
CPC .............. *A61F 2/885* (2013.01); *A61F 2/82* (2013.01); *A61F 2/88* (2013.01); *A61F 2/90* (2013.01); *A61F 2230/0054* (2013.01); *A61F 2250/0098* (2013.01)

(58) Field of Classification Search
CPC .............. A61F 2/82; A61F 2002/821; A61F 2002/825; A61F 2/86; A61F 2/88; A61F 2/885; A61F 2/90
See application file for complete search history.

(56) References Cited

U.S. PATENT DOCUMENTS

| | | |
|---|---|---|
| 4,430,083 A | 2/1984 | Ganz et al. |
| 4,722,344 A | 2/1988 | Cambron et al. |
| 5,045,072 A | 9/1991 | Castillo et al. |
| 5,047,050 A | 9/1991 | Arpesani |
| 5,258,020 A | 11/1993 | Froix |
| 5,320,100 A | 6/1994 | Herweck et al. |

(Continued)

*Primary Examiner* — Jonathan Miles
(74) *Attorney, Agent, or Firm* — Seager, Tufte & Wickhem, LLP

(57) ABSTRACT

The invention relates to an implantable radiopaque stent adapted to be disposed in a body lumen. In one aspect of the invention, a plurality of elongate filaments including one or more radiopaque filaments are arranged to form a hollow tubular structure having a tubular wall that defines an inner surface and an outer surface and opposing first open end and second open end. One of the open ends of the stent is formed by an intersection of adjacent filament ends. A radiopaque compound is applied to the intersection, the radiopaque compound comprising radiopaque material and polymeric material. The radiopaque compound and radiopaque filament provide improved external imaging of the tubular structure on imaging equipment.

20 Claims, 6 Drawing Sheets

(56) References Cited

U.S. PATENT DOCUMENTS

| | | |
|---|---|---|
| 5,607,442 A | 3/1997 | Fischell et al. |
| 5,800,511 A | 9/1998 | Mayer |
| 5,957,974 A | 9/1999 | Thompson et al. |
| 6,019,786 A * | 2/2000 | Thompson ............... A61F 2/06 606/191 |
| 6,048,362 A | 4/2000 | Berg |
| 6,077,880 A | 6/2000 | Castillo et al. |
| 6,162,244 A | 12/2000 | Braun et al. |
| 6,162,245 A * | 12/2000 | Jayaraman ............... A61F 2/07 623/1.15 |
| 6,174,329 B1 | 1/2001 | Callol et al. |
| 6,174,330 B1 | 1/2001 | Stinson |
| 6,200,338 B1 | 3/2001 | Solomon et al. |
| 6,217,609 B1 | 4/2001 | Haverkost |
| 6,287,331 B1 | 9/2001 | Heath |
| 6,395,326 B1 | 5/2002 | Castro et al. |
| 6,426,145 B1 | 7/2002 | Moroni |
| 6,572,644 B1 | 6/2003 | Moein |
| 6,626,936 B2 | 9/2003 | Stinson |
| 6,663,663 B2 | 12/2003 | Kim et al. |
| 6,669,724 B2 | 12/2003 | Park et al. |
| 7,041,126 B2 | 5/2006 | Shin et al. |
| 2001/0002416 A1 | 5/2001 | Matakawa et al. |
| 2001/0047199 A1 * | 11/2001 | Wijay ...................... A61F 2/91 623/1.15 |
| 2002/0007222 A1 * | 1/2002 | Desai ............... A61B 17/06109 623/23.65 |
| 2002/0138133 A1 | 9/2002 | Lenz et al. |
| 2003/0004563 A1 | 1/2003 | Jackson et al. |
| 2003/0040771 A1 * | 2/2003 | Hyodoh ................... A61F 2/90 606/200 |
| 2004/0054413 A1 | 3/2004 | Higham et al. |
| 2004/0088039 A1 | 5/2004 | Lee et al. |
| 2004/0148014 A1 | 7/2004 | Nuutinen et al. |
| 2004/0167496 A1 | 8/2004 | Poole et al. |
| 2005/0049682 A1 * | 3/2005 | Leanna .................... A61F 2/90 623/1.15 |
| 2005/0064223 A1 | 3/2005 | Bavaro et al. |
| 2005/0064224 A1 | 3/2005 | Bavaro et al. |
| 2005/0065434 A1 | 3/2005 | Bavaro et al. |
| 2006/0111771 A1 | 5/2006 | Ton et al. |
| 2006/0190070 A1 * | 8/2006 | Dieck ...................... A61F 2/90 623/1.12 |
| 2006/0265049 A1 | 11/2006 | Gray et al. |
| 2006/0276910 A1 | 12/2006 | Weber |

* cited by examiner

RADIOPAQUE COMPOSITIONS, STENTS AND METHODS OF PREPARATION

CROSS-REFERENCE TO RELATED APPLICATIONS

This application is a Continuation of U.S. application Ser. No. 13/853,181, filed Mar. 29, 2013, which is a Continuation of U.S. application Ser. No. 12/061,379 filed Apr. 2, 2008, now U.S. Pat. No. 8,409,270, which claims the benefit of U.S. Provisional Application No. 60/923,650 filed Apr. 16, 2007, the contents all of which are incorporated herein by reference.

FIELD OF THE INVENTION

The present invention generally relates to radiopaque compositions, and more particularly, to radiopaque stents and methods for making the same.

BACKGROUND OF THE INVENTION

Implantable stents are devices that are placed in a body structure, such as a blood vessel or body cavity, to provide support and to maintain the structure open. Generally, implantable stents comprise a flexible tubular body composed of several individual rigid but flexible filament elements. In some stents, the filaments extend in helix configuration with a center line of the tubular body about a common axis. Typically, the filaments are woven into braided configurations that impart stability to the tubular body. The filaments can be arranged symmetrically wherein the number of filaments in each direction of a braid is divisible by two. The greater the diameter of the tubular body, the more filaments are used to give stability to the body.

Generally, the proper deployment of a stent in a body cavity, such as the esophagus, requires a medical practitioner to follow movement of the stent through the body to the precise position at which the stent is to be deployed. To that end, radiopaque stents have been developed that allow the medical practitioner to track the position of the stent during movement through the body using fluoroscope and/or x-ray devices.

The opacity of a stent image tends to vary with the material and type of process used to create the stent. For example, radiopacity may be limited by the location of radiopaque materials in the stent. Furthermore, introducing radiopaque materials into stent filaments can produce undesirable mechanical alterations to filament mechanical properties.

As such, there exists a need for an improved radiopaque polymeric stent that has greater radiopacity yet maintains its overall functionality during and after various medical procedures.

SUMMARY OF THE INVENTION

The invention relates to an implantable radiopaque stent adapted to be disposed in a body lumen. In one aspect of the invention, a plurality of elongate filaments including one or more radiopaque filaments are arranged to form a hollow tubular structure having a tubular wall that defines an inner surface and an outer surface and opposing first open end and second open end. One of the open ends of the stent is formed by an intersection of adjacent filament ends. A radiopaque compound is applied to the intersection, the radiopaque compound comprising radiopaque material and polymeric material. The radiopaque compound and radiopaque filament provide improved external imaging of the tubular structure on imaging equipment.

The stent of this aspect of the invention desirably may have at least one radiopaque filament having a diameter greater than the diameter of non-radiopaque filaments.

The stent of this aspect of the invention desirably includes radiopaque material selected from the group consisting of gold, barium sulfate, ferritic particles, platinum, platinum-tungsten, palladium, platinum-iridium, rhodium, tantalum and combinations thereof. Preferably, the polymeric material is selected from the group consisting of polyester, polypropylene, polyethylene, polyurethane, polynaphthalene, polytetrafluoroethylene, expanded polytetrafluoroethylene, silicone, and combinations thereof.

The stent of this aspect of the invention desirably may have one of the open ends trimmed at the intersection prior to applying the radiopaque compound. Desirably, the radiopaque compound is applied to at least one trimmed end from an automated dispenser.

The stent of this aspect of the invention desirably may have one or more radiopaque filaments formed from a bioabsorbable material and a radiopaque material. Desirably, the bioabsorbable material is selected from the group consisting of poly-L-lactide, poly-D-lactide, polyglycolide, polydioxanone, polycaprolactone, polygluconate, polylactic acid-polyethylene oxide copolymers, modified cellulose, collagen, poly(hydroxybutyrate), polyanhydride, polyphosphoester, poly(amino acids), poly(alpha-hydroxy acid) and combinations thereof.

The stent of this aspect of the invention desirably may have one or more radiopaque filaments formed from a polymeric material and radiopaque material. Desirably, the polymeric material is selected from the group consisting of polyester, polypropylene, polyethylene, polyurethane, polynaphthalene, polytetrafluoroethylene, expanded polytetrafluoroethylene, silicone, and combinations thereof.

The stent of this aspect of the invention desirably may be treated with any of the following: anti-thrombogenic agents, anti-proliferative agents, anti-inflammatory agents, antineoplastic/antiproliferative/anti-miotic agents, anesthetic agents, anti-coagulants, vascular cell growth promotors, vascular cell growth inhibitors, cholesterol-lowering agents; vasodilating agents; agents which interfere with endogenous vascoactive mechanisms, and combinations thereof.

In another aspect of the present invention, a method for making a radiopaque stent is provided. The method includes the steps of arranging a plurality of elongated filaments comprising at least one radiopaque filament for permanent attachment to a hollow tubular structure in a linear direction traverse to a longitudinal length of the tubular structure, the tubular structure providing a tubular wall defining an interior surface and an exterior surface and having opposed open first and second ends, and applying a radiopaque compound to an intersection of adjacent filament ends located at one of the opposed open ends, the radiopaque compound comprising radiopaque material and polymeric material. The radiopaque compound and radiopaque filament improving external imaging of the tubular structure on imaging equipment.

The method of this aspect of the invention desirably may include forming one or more radiopaque filaments with a diameter greater than the diameter of each of the plurality of filaments.

The method of this aspect of the invention desirably may include arranging a plurality of elongate radiopaque filaments. Preferably, the plurality of radiopaque filaments are arranged in a helix configuration about a centerline of the tubular structure with a common axis.

The method of this aspect of the invention desirably may include forming the tubular structure by braiding the filaments. The method of this aspect of the invention also may include trimming at least one of the open ends at the intersection and applying the radiopaque compound to the intersection in a bulb shape. Preferably, the method of this aspect of the invention includes adding xylene to the radiopaque compound and dispensing the radiopaque compound from an automated dispenser to stent ends.

The method of this aspect of the invention may include selecting the radiopaque material from the group consisting of gold, barium sulfate, ferritic particles, platinum, platinum-tungsten, palladium, platinum-iridium, rhodium, tantalum and combinations thereof. Preferably, the method also includes selecting the polymeric material from the group consisting of polyester, polypropylene, polyethylene, polyurethane, polynaphthalene, polytetrafluoroethylene, expanded polytetrafluoroethylene, silicone, and combinations thereof.

The method of this aspect of the invention also may include forming the at least one radiopaque filament from a bioabsorbable material and a radiopaque material. Preferably, the method includes adapting the bioabsorbable material degrade in vivo, and selecting the bioabsorbable material from the group consisting of poly-L-lactide, poly-D-lactide, polyglycolide, polydioxanone, polycaprolactone, polygluconate, polylactic acid-polyethylene oxide copolymers, modified cellulose, collagen, poly(hydroxybutyrate), polyanhydride, polyphosphoester, poly(amino acids), poly (alpha-hydroxy acid) and combinations thereof.

The method of this aspect of the invention also may include treating the tubular structure with pharmaceuticals selected from the group consisting of anti-thrombogenic agents, anti-proliferative agents, anti-inflammatory agents, antineoplastic/antiproliferative/anti-miotic agents, anesthetic agents, anti-coagulants, vascular cell growth promotors, vascular cell growth inhibitors, cholesterol-lowering agents; vasodilating agents; and agents which interfere with endogenous vascoactive mechanisms.

The stents and methods of the present invention may be used at strictures or damaged vessel sites. Such sites may suitably include bodily tissue, bodily organs, vascular lumens, non-vascular lumens and combinations thereof, such as, but not limited to, in the coronary or peripheral vasculature, esophagus, trachea, bronchi, colon, small intestine, biliary tract, urinary tract, prostate, brain, stomach and the like The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the claims and equivalents thereof. The foregoing aspects and other attendant advantages of the present invention will become more readily appreciated by the detailed description taken in conjunction with the accompanying drawings.

BRIEF DESCRIPTION OF THE DRAWINGS

Like reference symbols in the various drawings indicate like elements.

DETAILED DESCRIPTION OF THE PREFERRED EMBODIMENTS

Figure 1:
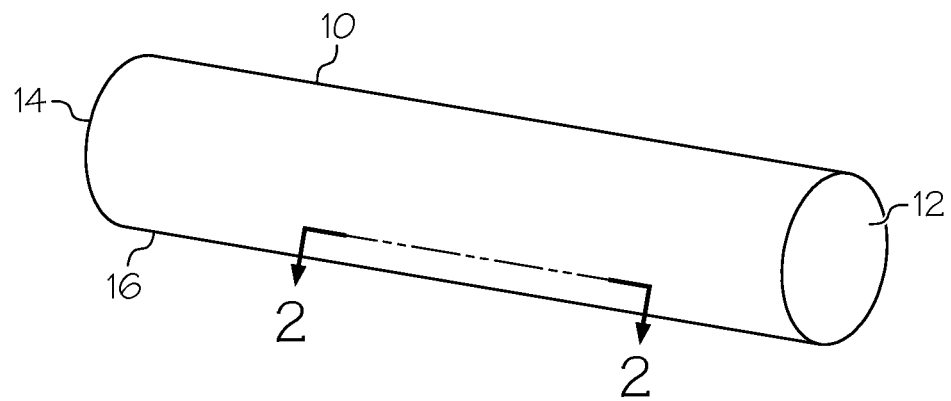
FIG. 1 is a perspective view of a hollow, tubular stent according to the present invention.
Figure 2:
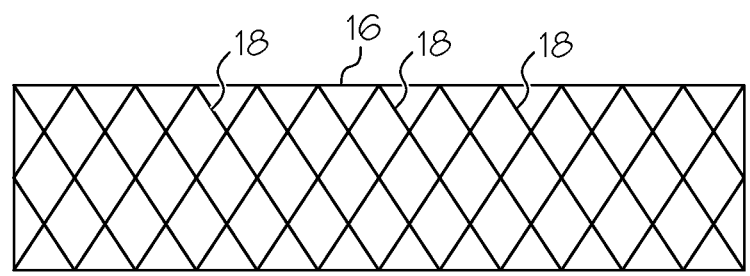
FIG. 2 is an expanded view of a wall portion of the stent of FIG. 1 taken along the 2-2 axis showing a plurality of stent filaments.

FIG. 1 depicts a stent 10 according to the present invention. As shown in FIG. 1, the stent 10 includes a hollow tubular structure having opposed open ends 12, 14 and a tubular wall 16 defining an inner surface and an outer surface. A portion 2-2 of the tubular wall 16 is shown in FIG. 2 having a plurality of filaments or threads 18 permanently attached to the tubular wall 16. The elongate filaments 18 traverse the length of the stent 10 in a direction traverse to the longitudinal length of the stent 10. The filaments 18 may be formed into the tubular wall 16 by braiding the filaments 18, winding the filaments 18, knitting the filaments 18, twisting the filaments, and combinations thereof. In some preferred embodiments, the filaments 18 are braided to form the tubular wall 16.

As used herein the term braiding and its variants refer to the diagonal intersection of elongate filaments, such as elongate wires, so that each filament passes alternately over and under one or more of the other filaments, which is commonly referred to as an intersection repeat pattern. Useful braiding patterns include, but are not limited to, a diamond braid having a 1/1 intersection repeat pattern, a regular braid having a 2/2 intersection repeat pattern or a hercules braid having a 3/3 intersection repeat pattern.

Figure 3A:
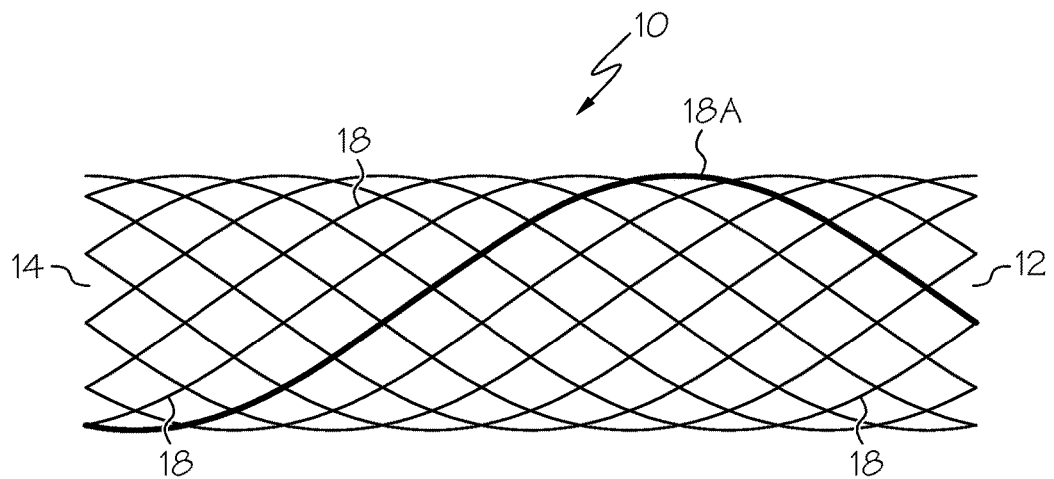
FIG. 3A depicts a braided stent having a weld according to the present invention.

Referring now to FIG. 3A, an example thirty-six (36) filament braided stent 10 according to the present invention is disclosed. As shown in FIG. 3A, in one preferred embodiment, the filaments 18 are braided in a helix pattern about a centerline of the tubular structure with a common axis. In another preferred embodiment, the filaments 18 are braided to form the tubular structure.

As shown in FIG. 3A, the stent 10 includes open ends 12, 14 and filaments 18 (e.g., wires) that are fully or partially composite filaments 18. The open ends 12, 14 and filaments 18 preferably enhance visibility of the stent in the body when using external imaging. Desirably, the enhanced visibility is enhanced radiopacity to provide improved fluoroscopic or x-ray visualization of the filaments 18 and ends 12, 14 in the body. Enhanced radiopacity may be achieved by using the below-described radiopaque materials in combination with biocompatible stent material.

Radiopaque materials are believed to be more visible under fluoroscopic or x-ray visualization due to their higher density than corresponding biocompatible stent material. The present invention, however, is not limited to a stent with improved fluoroscopic or x-ray visualization. For example, the stent 10 may also have improved external imaging under magnetic resonance imaging (MRI) and/or ultrasonic visualization techniques. Magnetic resonance imaging is produced by complex interactions of magnetic and radio frequency fields. Materials for enhancing MRI visibility include, but are not be limited to, metal particles of gadolinium, iron, cobalt, nickel, dysprosium, dysprosium oxide, platinum, palladium, cobalt based alloys, iron based alloys, stainless steels, or other paramagnetic or ferromagnetic metals, gadolinium salts, gadolinium complexes, gadopentetate dimeglumine, compounds of copper, nickel, manganese, chromium, dysprosium and gadolinium. To enhance the visibility under ultrasonic visualization, the stent 10 of the present invention may include ultrasound resonant material, such as but not limited to gold.

In one preferred embodiment, for example, the filaments 18 of the stent 10 are made from a biocompatible material or biocompatible materials. Useful biocompatible materials include biocompatible metals, biocompatible alloys and biocompatible polymeric materials, including synthetic biocompatible polymeric materials and bioabsorbable or biodegradable polymeric materials. Desirably, the filaments 18 are biocompatible metals or alloys made from, but not limited to, nitinol, stainless steel, cobalt-based alloy such as Elgiloy, platinum, gold, titanium, tantalum, niobium, polymeric materials and combinations thereof. Useful synthetic biocompatible polymeric materials include, but are not limited to, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, silks and polytetrafluoroethylenes. The polymeric materials may further include a metallic, a glass, ceramic or carbon constituent or fiber. Useful and nonlimiting examples of bioabsorbable or biodegradable polymeric materials include poly(L-lactide) (PLLA), poly(D,L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), polyphosphate ester) and the like.

Filaments 18 also may be made from polymeric materials that include radiopaque materials. In one preferred embodiment, radiopaque materials, such as metallic-based powders, ceramic-based powders, particulates or pastes, are incorporated into the polymeric material. Preferably, the radiopaque material is blended with the polymer composition and subsequently fashioned into the stent. For example, a radiopaque powder may be added to the polymeric material at extrusion time using a double screw extruder to form stent filaments. The radiopaque powder typically includes at least one element having a high atomic number such as bismuth, barium, tantalum, tungsten, gold, platinum.

As shown in FIG. 3A, in one preferred embodiment, the filaments 18 include at least one radiopaque filament 18a that is formed by compounding approximately 25 to 50% or higher weight of radiopaque material with polymeric material. Preferably, one or more radiopaque filaments are formed having a diameter greater than the diameter of non-radiopaque filaments. For example, in one preferred embodiment, the non-radiopaque filaments 18 are relatively thin at a diameter of about 0.011 inches whereas one or more formed radiopaque filaments 18a have a diameter greater than 0.011 inches. The number of filaments and the diameters of the filaments, which may be the same or different, are not limiting, and other numbers of filaments and other filament diameters may suitably be used. Furthermore, the outer surface of radiopaque filaments are courser than the outer surface of non-radiopaque filaments due to the inclusion of radiopaque material included therein. Desirably, an even number of filaments are used, for example from about 10 to about 36 wires.

In one preferred embodiment, the radiopaque filaments of the present invention include a longitudinal outer member concentrically disposed about a central core that extends along an axis of the outer member. Preferably, the outer member is formed of a metal, such as nitinol, that exhibits desirable properties, such as high elasticity and biocompatibility. The surface of the outer member may include a non-metal coating of, e.g., fluorocarbons, silicones, hydrophilic and lubricous biocompatible materials. The central core of the radiopaque filaments includes a metal, such as tantalum, with a density greater than the longitudinal member to enhance the radiopacity of the filament and thus the stent from which it is formed. Preferably, the core is bonded to and substantially enclosed by the outer member such that the core does not have any substantial exposed surface and therefore does not contact body tissue when positioned within the body during use. In one preferred embodiment, the core is formed as a continuous solid member in intimate contact with and bonded to the interior portions of the outer member without the formation of substantial voids between the core and outer member. The core material preferably enhances the radiopacity of the filament but preferably does not substantially affect the mechanical performance of the filament.

In another preferred embodiment, the radiopaque filaments are formed as composite filaments including a central radiopaque core, an outer member, and an intermediate member between the core and the outer member. The intermediate member provides a barrier between the core and the outer member, and may be useful in composite filaments employing core and outer member materials that would be incompatible if contiguous, e.g. due to a tendency to form intermetallics.

In yet another preferred embodiment, the radiopaque filaments are formed as composite elements having a central radiopaque core, a structural outer member and a relatively thin annular outer cover layer. Suitable materials for the cover layer include tantalum, platinum, iridium, niobium, titanium and stainless steel.

Several advantages may be present by forming one or more radiopaque filaments with a diameter greater than non-radiopaque filaments. For example, the larger diameter of the radiopaque filament may be clearly visible under external imaging equipment, such as x-ray and fluoroscope equipment. In addition, when the stent is braided with a radiopaque filament in a spiral shape about the stent, the larger diameter of the radiopaque filament may extend outward from the outer surface of the tubular structure due to the radiopaque filament's larger diameter and thereby reduce migration of the stent in a body lumen. Furthermore, the coarseness of the radiopaque filament outer surface compared to that of non-radiopaque filaments, may further secure the stent to the body lumen and reduce stent migration in the body.

As shown in the FIG. 3A example, the elongate filaments 18 terminating at open end 12 are mated and adjacently mated filaments are secured to one and the other by welds 20 or by other suitable means. For example, the filaments 18 may be welded together through use of a radiopaque welding material or the filaments 18 may be heatingly and/or meltably fused together without the use of a welding material. Further, the filaments 18 may be mechanically joined through the use of a small-sized or micro-fabricated clamp, crimpable tube, hypotube, and the like. The joining of three adjacently mated filaments 18 and the welding thereat is depicted in further detail in FIGS. 4-6. The positioning of adjacently mated filaments to form closed-loop end designs is further described in U.S. application Ser. No. 60/472,929, filed May 23, 2003, which was filed May 24, 2004 as U.S. application Ser. No. 10/852,495 and published as U.S. Patent Application Publication No. 2005/0049682 A1, the contents of all of which are incorporated herein by reference.

Figure 3B:
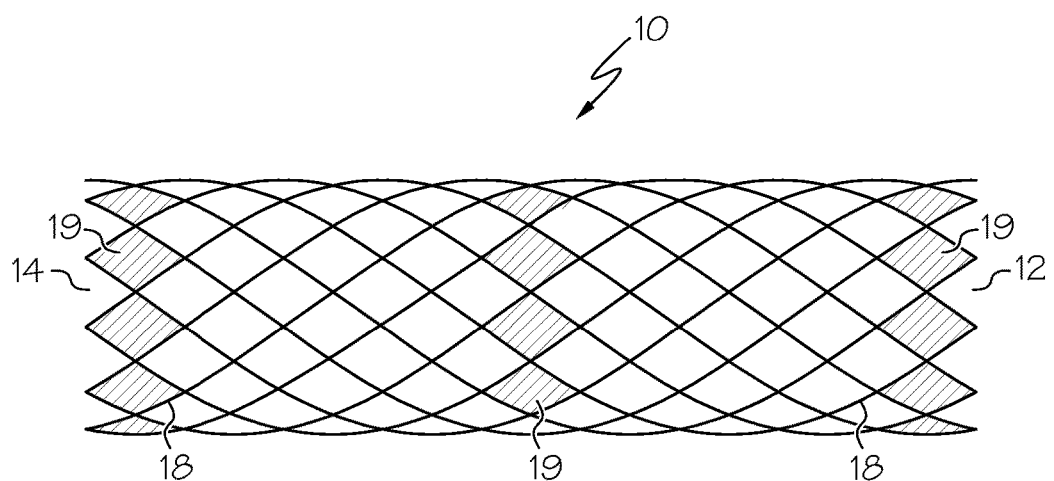
FIG. 3B depicts a braided stent with a closed-end loop design having a plurality of welds at the closed end according to the present invention.
Figure 3C:
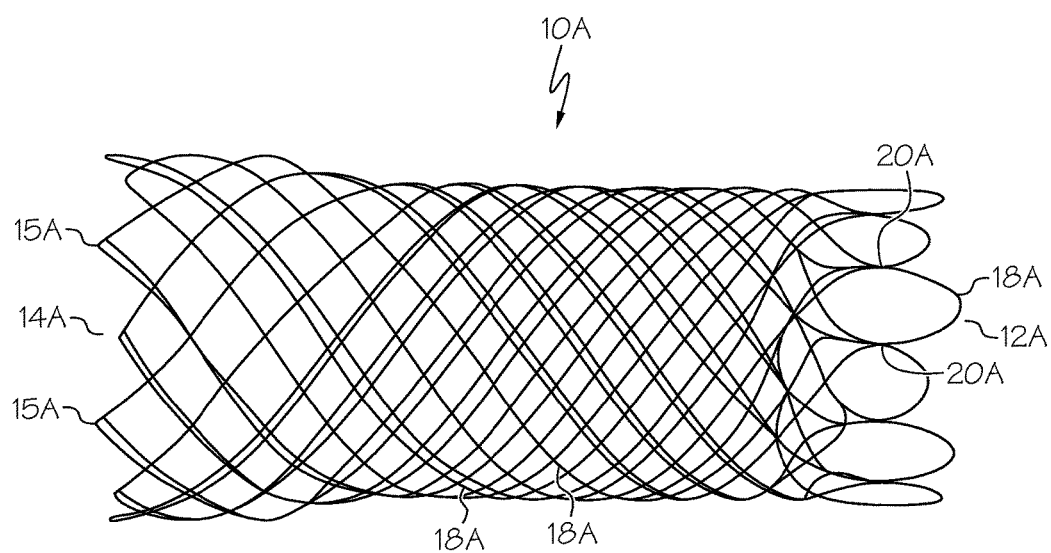
FIG. 3C depicts a braided stent having a radiopaque marker.

Referring now to FIG. 3C, in one preferred embodiment, a stent 10A of the present invention includes atraumatic open ends 12, 14. As used herein, the phrase "atraumatic end" and it variants refer to a terminal end of a stent which is free of sharp filament ends or other sharp projections or deformities which may cause trauma when implanted into a bodily lumen. For example, as shown in FIG. 3C, open end 14 of the stent 10A is atraumatic because the stent 10A is braided such that no ends of filaments 18A end at this end of the stent 10A. In other words, the stent 10A may be braided such that all the ends of the filaments 18A are distal from the end 14, for example, by commencing the braiding of the stent 10A with filaments 18A that are bent in a smooth configuration so that the loop ends 15A of the end 14A have no sharp or traumatically pointed bends or projections. Moreover, as described in further detail below, the end 12A of the stent 10A is atraumatic because, among other things, even though the filaments 18A terminate proximal to the end 14A of the stent 10A, certain filaments 18A may extend and loop back to provide an atraumatic end with, for example, no sharp or traumatically pointed bends, no sharp filament ends, no other traumatically sharp projections or deformities and the like.

Useful welding techniques include, but are not limited to, laser welding, electron beam welding, resistance welding, tungsten inert gas welding, metal inert gas welding and combinations thereof. In laser and electron beam welding the wires are partially melted by the energy provided by the laser or electron beam. In gas tungsten arc welding (GTAW or TIG welding), an arc is formed between an electrode, typically tungsten, and the metal being welded.

In metal inert gas (MIG) welding, an arc is generated between a filler electrode and the metal being welded with metal melted from the filler electrode being added to the metal being welded. Resistance welding uses the application of electric current and sometimes mechanical pressure to create a weld between two pieces of metal. The weld areas may be shielded with an inert gas. Suitable, but non-limiting, inert gasses include argon and argon/gas admixtures, such as argon/hydrogen or argon/helium.

Figure 4:
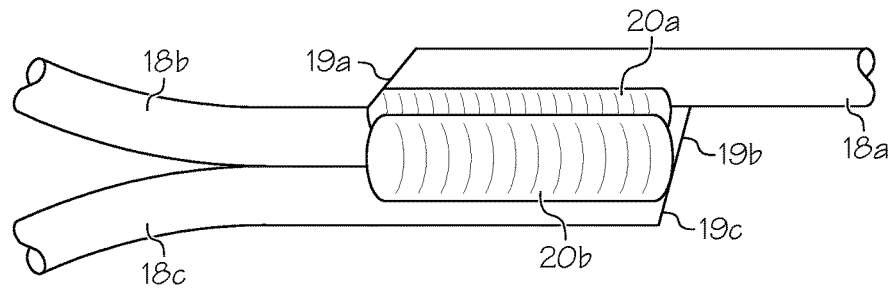
FIGS. 4 and 5 are expanded views of weld areas of FIG. 3B illustrating smooth terminated filament ends.
Figure 5:
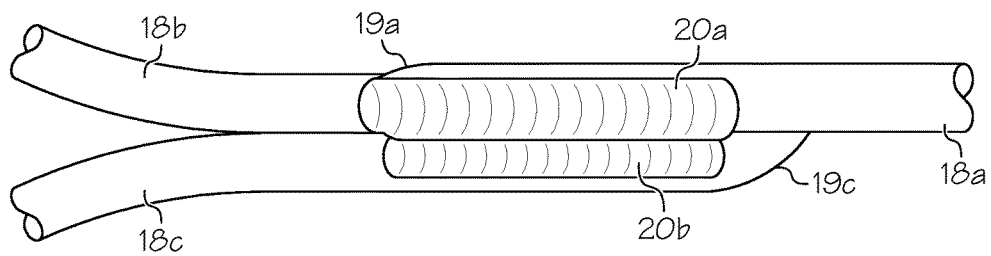
Figure 6:
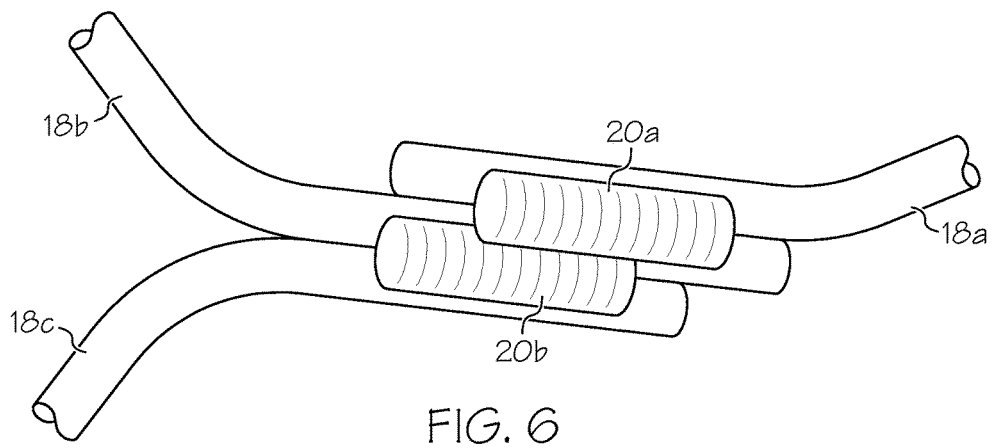
FIG. 6 is an expanded view of the weld of FIG. 3B showing a pair of offset welds joining three adjacently juxtaposed filament wires.

Adjacently welded filaments according to the present invention are depicted in FIGS. 4-6. The terminated filament ends 19a, 19b and 19c are trimmed to remove sharp edges from the ends. In one preferred embodiment, as depicted in FIG. 4, terminal filament ends 19b and 19c are cut to remove shape edges. Further, as depicted in FIG. 5, terminal filament end 19a is trimmed to a have a curved portion or a portion having a radius of curvature. Such trimming may be achieved by use of a laser beam over the terminal end 19a. Heat generated by the laser beam melts the filament material forming a smooth, curved shape. Surface tension of the molten wire material allows the material to flow out evenly. These techniques for trimming the terminal filament ends may be used individually or in combination. In other words, terminal ends 19a, 19b and 19c may be, individually or in combination, trimmed and/or partially melted to provide a smooth terminal filament end. Additionally, the terminal filament ends 19a, 19b and 19c may be chemically or electro-chemically treated to remove sharp ends. Details of chemically or electro-chemically removing processes are described in U.S. patent application Ser. No. 10/845,844, filed May 14, 2004, the contents of which are incorporated herein by reference.

In one preferred embodiment, radiopaque material and polymeric material, as described previously, are mixed with a small amount of xylene to facilitate flow of the mixed radiopaque polymeric material from a dispenser. For example, as shown in FIG. 3A, in one preferred embodiment, the radiopaque polymeric material is applied from the dispenser to stent ends 12, 14 in a bulb shape at the intersection of filaments after filament end trimming. As a result, the radiopacity of the stent is increased.

In another preferred embodiment, referring now to FIG. 3B, the radiopaque polymeric material is applied from the dispenser to one or more recesses 19 formed by the intersection of filaments 18. As shown in FIG. 3B, a plurality of recesses 19 may be filled with the radiopaque material and form one or more radiopaque markers. In one preferred embodiment, the radiopaque material is designed to disperse from the stent 10 after a predetermined period of time. Of course, it will be appreciated by one skilled in the art that the radiopaque material of the present invention may be applied in various stent configurations having hollow, cavity, porous portions, or combinations thereof.

Referring now to FIGS. 4-5, a securably joined region or weld 20a joins filaments 18a and 18b, and a securably joined region or weld 20b joins filaments 18b and 18c. Securably joined regions or welds 20a and 20b are depicted as substantially overlapping one and the other. The present invention, however, is not so limited. As depicted in FIG. 6, a securably joined region or weld 20a may be longitudinally offset from a securably joined region or weld 20b. Desirably, the length of the securably joined regions or welds 20a and 20b are substantially similar. Also desirably, a portion of a securably joined region or weld 20a overlaps a portion of a securably joined region or weld 20b. Such offsetting and/or overlapping of the securably joined regions or welds may provide greater fatigue life. In one preferred embodiment, a radiopaque polymeric material is applied to the secured joined regions to further enhance radiopacity of the stent.

Figure 7:
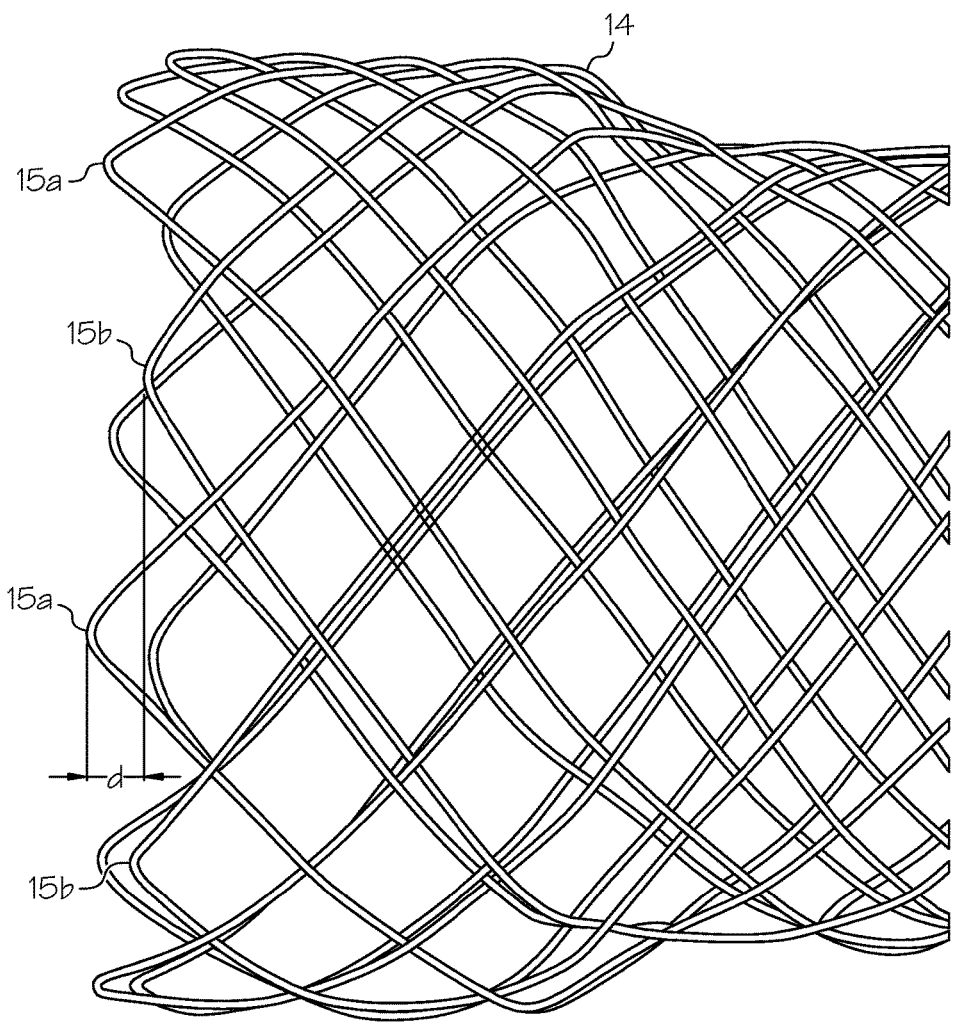
FIG. 7 depicts an exploded, partial view of the left-side stent end of FIG. 3B.

In one preferred embodiment, referring now to FIG. 7, which is a partial exploded view of a portion of the stent end 14 of FIG. 3C, stent loops 15a may be staggered from stent loops 15b. The staggering of the loops results in a longitudinal offset, d, between apexes or apices of adjacent loops. As depicted in FIG. 7, one set of loops 15a are offset from another set of loops 15b by a single longitudinal offset, d. The present invention, however, is not so limited. For example, the stent end 14 may have staggered loop ends having more than one or a plurality of longitudinal offsets. The staggered loop ends 15a, 15b with either a single offset or a plurality of offsets may suitably be formed by providing a mandrel with longitudinally offset pins (not shown) and commencing braiding or otherwise positioning the stent wires thereat. The staggered loop ends 15a, 15b then may be covered with a radiopaque polymeric material to further enhance radiopacity of the stent 10.

Figure 8:
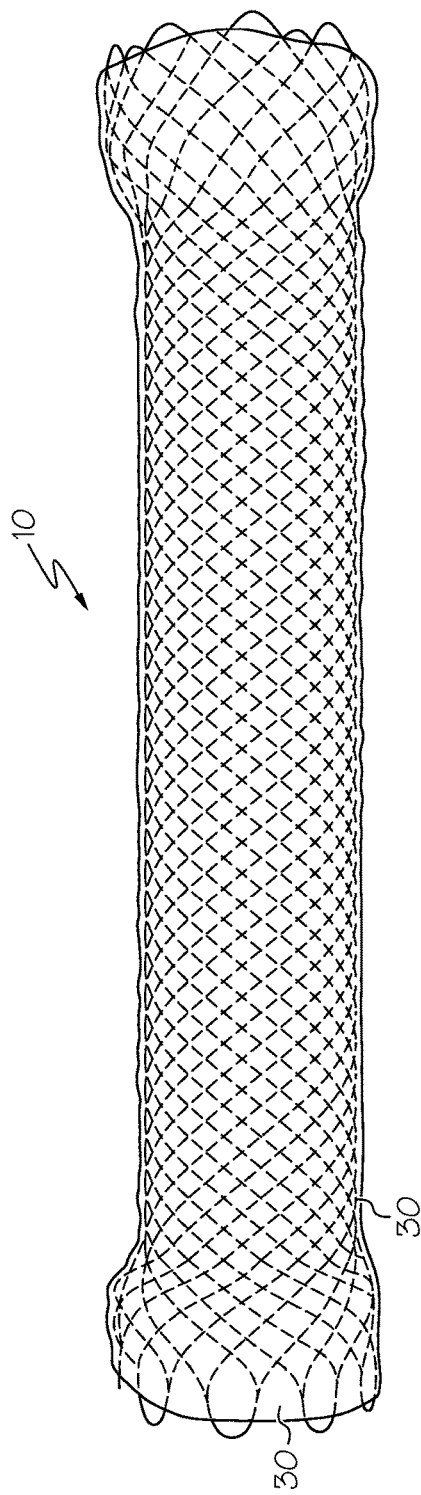
FIG. 8 depicts a stent having a covering of radiopaque polymeric material according to the present invention.

Referring now to FIG. 8, the stent 10 may be fully, substantially or partially covered with a radiopaque polymeric material 30. The covering may be in the form of a tubular structure. One nonlimiting example of a polymeric material is silicone. For example, in one preferred embodiment, the stent is covered with a silicon covering solution comprising a mixture of radiopaque powder. In this preferred embodiment, radiopaque particles included in the powder are incorporated into the covering providing improved radiopacity. Preferably, the covering is formed by dip coating the stent in a self-solidifying fluid. Upon solidifying, the covering preferably has a thickness less than the diameter of the filaments resulting in a structure surface defined by the filaments.

In another preferred embodiment, radiopaque material is added to the silicon covering solution by metallurgically alloying or by making clad composite structures Radiopaque material also may be filled into hollow cores, cavities or pores in the polymer matrix as discussed in connection with FIG. 3B previously. Organic radiopaque powders containing elements or salts or oxides of elements such as bromine, iodine, iodide, barium, and bismuth also may be used instead of metal powders.

Figure 10:
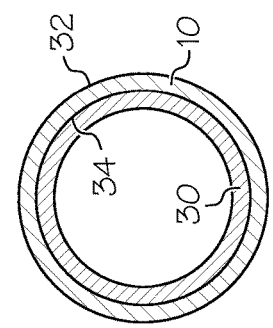
FIG. 10 is a cross-sectional view of the stent of FIG. 8 showing an inner covering of radiopaque polymeric material about the stent.
Figure 9:
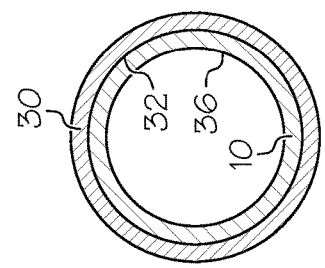
FIG. 9 is a cross-sectional view of the stent of FIG. 8 showing an outer covering of radiopaque polymeric material about the stent.

The radiopaque polymeric material 30 may be disposed on external surfaces 32 of the stent 10, as depicted in FIG. 9, or disposed on the internal surfaces 34 of the stent 10, as depicted in FIG. 10, or combinations thereof. The silicone covering may be suitably formed by dip coating the stent. The present invention is not limited to forming the silicone film by dip coating, and other techniques, such as spraying, may suitably be used. After applying the radiopaque silicone coating or film to the stent, the silicone may be cured. Desirably, the curing is low temperature curing, for example from about room temperature to about 90° C. for a short period of time, for example from about 10 minutes or more to about 16 hours. The cured radiopaque silicone covering may also be sterilized by electronic beam radiation, gamma radiation ethylene oxide treatment and the like. Further details of the curing and/or sterilization techniques may be found in U.S. patent application Ser. No. 6,099,562, the content of which is incorporated herein by reference. Argon plasma treatment of the cured silicone may also be used.

With any embodiment of the stent 10 of the present invention, the stent may be usable to maintain patency of a bodily vessel, such as in the coronary or peripheral vasculature, esophagus, trachea, bronchi, colon, biliary tract, urinary tract, prostate, brain, and the like. Also, the stent 10 may be treated with any of the following pharmaceuticals: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethylketon, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

Further, with any embodiment of the stent 10, the general tubular shape may be varied. For example, the tubular shape may have a varied diameter, an inwardly flared end, an outwardly flared end and the like. Further, the ends of the stent may have a larger diameter than the middle regions of the stent. A braided stent with outwardly flared ends is further described in U.S. Pat. No. 5,876,448, the contents of which are incorporated herein by reference.

In one aspect of the present invention, an implantable stent is provided. The implantable radiopaque stent includes a plurality of elongate filaments including at least one radiopaque filament. The plurality of filaments are arranged to form a hollow tubular structure having a tubular wall that defines an inner surface and an outer surface and opposing first open end and second open end. Desirably, at least one of the open ends is formed by an intersection of adjacent filament ends and application of a radiopaque compound to the intersection. The radiopaque compound includes radiopaque material and polymeric material, wherein the radiopaque compound and the radiopaque filament improve external imaging of the tubular structure on imaging equipment.

Desirably, the stent of this aspect of the present invention desirably may also have at least one radiopaque filament has a diameter greater than the diameter of each of the plurality of filaments. Preferably, the implantable stent comprises a plurality of elongate radiopaque filaments.

The stent of this aspect of the present invention desirably may also have the plurality of radiopaque filaments are arranged in a helix configuration about a centerline of the tubular structure with a common axis. The stent of this aspect of the present invention desirably may also have the filaments braided to form the tubular structure.

The stent of this aspect of the present invention may also have at least one of the open ends is trimmed at the intersection. The stent of this aspect of the present invention may also have the radiopaque compound applied from an automated dispenser to the intersection in a bulb shape. Preferably, the radiopaque compound includes silicone.

The stent of this aspect of the present invention includes a radiopaque compound comprising a radiopaque powder or paste. Desirably, the radiopaque compound also includes comprises xylene. Preferably, the radiopaque compound comprises at least twenty-five percent of the radiopaque material and the imaging equipment is at least one of fluoroscope and x-ray equipment.

Desirably, the stent of this aspect of the present invention includes a radiopaque material selected from the group consisting of gold, barium sulfate, ferritic particles, platinum, platinum-tungsten, palladium, platinum-iridium, rhodium, tantalum and combinations thereof.

The stent of this aspect of the present invention preferably includes polymeric material selected from the group consisting of polyester, polypropylene, polyethylene, polyurethane, polynaphthalene, polytetrafluoroethylene, expanded polytetrafluoroethylene, silicone, and combinations thereof.

Desirably, the implantable radiopaque includes at least one radiopaque filament having a bioabsorbable material and a radiopaque material. Preferably, the bioabsorbable material is also adapted to degrade in vivo.

The stent of this aspect of the invention includes bioabsorbable material selected from the group consisting of poly-L-lactide, poly-D-lactide, polyglycolide, polydioxanone, polycaprolactone, polygluconate, polylactic acid-polyethylene oxide copolymers, modified cellulose, collagen, poly(hydroxybutyrate), polyanhydride, polyphosphoester, poly(amino acids), poly (alpha-hydroxy acid) and combinations thereof.

Desirably, the stent of this aspect of the invention includes a radiopaque filament having a polymeric material and a radiopaque material.

The stent of this aspect of the invention preferably includes the tubular structure covered with a polymeric material. Desirably, the polymeric material includes radiopaque particles.

The stent of this aspect of the present invention preferably includes the tubular structure being treated with pharmaceuticals selected from the group consisting of anti-thrombogenic agents, anti-proliferative agents, anti-inflammatory agents, antineoplastic/antiproliferative/anti-miotic agents, anesthetic agents, anti-coagulants, vascular cell growth promotors, vascular cell growth inhibitors, cholesterol-lowering agents; vasodilating agents; and agents which interfere with endogenous vascoactive mechanisms.

In another aspect of the present invention, a method for making an implantable stent includes arranging a plurality of elongated filaments comprising at least one radiopaque filament for permanent attachment to a hollow tubular structure in a linear direction traverse to a longitudinal length of the tubular structure. The tubular structure providing a tubular wall defining an interior surface and an exterior surface and having opposed open first and second ends.

The method of this aspect of the invention may include applying a radiopaque compound to an intersection of adjacent filament ends located at one of the opposed open ends. The radiopaque compound including radiopaque material and polymeric material, wherein the radiopaque compound and the radiopaque filament improve external imaging of the tubular structure on imaging equipment.

The method of this aspect of the present invention may further include the step of forming the at least one radiopaque filament with a diameter greater than the diameter of each of the plurality of filaments.

The method of this aspect of the present invention may further include the step of arranging a plurality of elongate radiopaque filaments. The method also may further include arranging the plurality of radiopaque filaments in a helix configuration about a centerline of the tubular structure with a common axis.

The method of this aspect of the present invention may also include the steps of forming the tubular structure by braiding the filaments, trimming at least one of the open ends at the intersection, applying the radiopaque compound to the intersection in a bulb shape, dispensing the radiopaque compound from an automated dispenser, compounding silicon into the radiopaque compound, and forming the radiopaque compound from at least one of a radiopaque powder and paste. The method of this aspect of the invention may also include adding xylene to the radiopaque compound.

Desirably, the method of this aspect includes at least twenty-five percent of the radiopaque compound having radiopaque material.

The method of this aspect of the invention also may include imaging equipment wherein at least one of the imaging equipment is fluoroscope and x-ray equipment.

The method of this aspect may further include the step of selecting the radiopaque material from the group consisting of gold, barium sulfate, ferritic particles, platinum, platinum-tungsten, palladium, platinum-iridium, rhodium, tantalum and combinations thereof.

Desirably, the method of this aspect also may include selecting the polymeric material from the group consisting of polyester, polypropylene, polyethylene, polyurethane, polynaphthalene, polytetrafluoroethylene, expanded polytetrafluoroethylene, silicone, and combinations thereof.

The method of this aspect may further include forming the at least one radiopaque filament from a bioabsorbable material and a radiopaque material. The method of this aspect may further include adapting the bioabsorbable material to degrade in vivo.

The method of this aspect of the invention may include the step of selecting the bioabsorbable material from the group consisting of poly-L-lactide, poly-D-lactide, polyglycolide, polydioxanone, polycaprolactone, polygluconate, polylactic acid-polyethylene oxide copolymers, modified cellulose, collagen, poly(hydroxybutyrate), polyanhydride, polyphosphoester, poly(amino acids), poly (alpha-hydroxy acid) and combinations thereof.

The method of this aspect of the invention also may include forming the at least one radiopaque filament from a polymeric material and a radiopaque material and covering the tubular structure with a polymeric material. The method also may include forming the polymeric material from radiopaque particles.

The method of this aspect of the invention may further include treating the tubular structure with pharmaceuticals selected from the group consisting of anti-thrombogenic agents, anti-proliferative agents, anti-inflammatory agents, antineoplastic/antiproliferative/anti-miotic agents, anesthetic agents, anti-coagulants, vascular cell growth promotors, vascular cell growth inhibitors, cholesterol-lowering agents; vasodilating agents, agents which interfere with endogenous vascoactive mechanisms, and combinations thereof.

The invention being thus described, it will now be evident to those skilled in the art that the same may be varied in many ways. Such variations are not to be regarded as a departure from the spirit and scope of the invention and all such modifications are intended to be included within the scope of the following claims.

What is claimed is:

1. A stent comprising:
  a plurality of elongate filaments, the plurality of filaments are braided or woven to form a hollow tubular structure having a tubular wall that defines an inner surface and an outer surface and opposing first open end and second open end;
  the braided or woven hollow tubular structure comprises a plurality of recesses formed by a plurality of intersections of the braided or woven plurality of filaments; and
  a composition comprising polymeric material disposed within each of one or more of the plurality of recesses in a pattern that extends circumferentially around the entire stent in two or more bands of filled recesses, wherein each of the filled recesses of the two or more bands is completely filled with the polymeric material, wherein the two or more bands each include an circumferential edge having alternating peaks and valleys, wherein the peaks of each of the two or more bands are located closer to the first open end than its valleys, and wherein the two or more bands are separated by one or more circumferential bands of unfilled recesses.

2. The stent of claim 1 wherein the first open end and second open end are atraumatic and free of any sharp filament ends.

3. The stent of claim 1 wherein all of the elongate filaments terminate at the first open end.

4. The stent of claim 1 wherein adjacent ends of the plurality of filaments are welded together with a welding material proximate the first open end.

5. The stent of claim 4 wherein the adjacent ends of the plurality of filaments are welded with a radiopaque welding material.

6. The stent of claim 1 wherein adjacent ends of the plurality of filaments are fused together by heat proximate the first open end.

7. The stent of claim 1 wherein the filaments are joined with a mechanical device selected from the group consisting of clamps, crimpable tubes and a hypotube.

8. The stent of claim 1 wherein the plurality of filaments are arranged symmetrically.

9. The stent of claim 8 wherein the number of filaments in each direction of a braid is divisible by two.

10. The stent of claim 1 wherein the stent comprises a terminal proximal end, a terminal distal end and a central portion and wherein the composition is provided within a plurality of recesses that define the terminal distal and proximal ends, and within a plurality of recesses that define the central portion of the stent with first and second circumferential bands of unfilled recesses located on opposite ends of the composition in the recesses in the central portion.

11. The stent of claim 1 comprising a proximal end and a distal end, at least one of which comprises an outward flare.

12. The stent of claim 1 further comprising a radiopaque material in the polymeric composition.

13. The stent of claim 1 wherein the composition comprises at least one polymeric material selected from the group consisting of polyester, polypropylene, polyethylene, polyurethane, polynaphthalene, polytetrafluoroethylene, expanded polytetrafluoroethylene, silicone, and combinations thereof.

14. The stent of claim 1 wherein the plurality of filaments are arranged helically about a centerline of the tubular structure with a common axis.

15. The stent of claim 1 wherein said stent is a coronary stent, a peripheral vasculature stent, an esophageal stent, a tracheal stent, a bronchial stent, a colonic stent, a stent for a small intestine, a biliary tract stent, a urinary tract stent, a prostate stent, a brain stent and a stomach stent.

16. The stent of claim 1, wherein the plurality of elongate filaments include first filaments having a first diameter and at least a second filament having a second diameter, wherein the second diameter is greater than the first diameter.

17. The stent of claim 1, wherein the two or more bands of filled recesses include a first band of filled recesses disposed at the first open end and a second band of filled recesses disposed at the second open end, wherein the first and second open ends are terminal open ends of the stent.

18. The stent of claim 17, further comprising a third band of filled recesses disposed in a central portion of the hollow tubular structure, the third band of filled recesses separated from the first and second bands of filled recesses by first and second circumferential bands of unfilled recesses located on opposite ends of the third band of filled recesses.

19. The stent of claim 18, wherein the first and second open ends include flared portions having diameters greater than a diameter of the central portion, wherein the first and second bands of filled recesses and the first and second bands of unfilled recesses are disposed on the flared portions, and the third band of filled recesses extends circumferentially around the central portion between the flared portions.

20. A stent comprising:
a plurality of elongate filaments, the plurality of filaments are braided or woven to form a hollow tubular structure having a tubular wall that defines an inner surface and an outer surface and opposing first and second terminal open ends;
the braided or woven hollow tubular structure comprises a plurality of recesses formed by a plurality of intersections of the braided or woven plurality of filaments; and
a composition comprising polymeric material disposed within and completely filling each of one or more of the plurality of recesses in a pattern that extends circumferentially around the entire stent in a first band of filled recesses at the first terminal open end, a second band of filled recesses at the second terminal open end, and a third band of filled recesses in a central portion of the tubular structure, wherein the first, second and third bands of filled recesses are separated by first and second circumferential bands of unfilled recesses located on opposite ends of the third band of filled recesses.

* * * * *